United States Patent [19]

Clausen et al.

[11] Patent Number: 5,753,458
[45] Date of Patent: May 19, 1998

[54] ACYLATION METHOD FOR PENICILLINS AND CEPHALOSPORINS

[75] Inventors: Kim Clausen, Tølløse; Annette Nielsen, Måløv; Niels Petersen, Skibby; Alexander Nikolov, Malmö, all of Denmark

[73] Assignee: Gist-Brocades B.V., Netherlands

[21] Appl. No.: 596,166

[22] PCT Filed: Jun. 12, 1995

[86] PCT No.: PCT/EP95/02277

§ 371 Date: Jan. 7, 1996

§ 102(e) Date: Jan. 7, 1996

[87] PCT Pub. No.: WO95/34675

PCT Pub. Date: Dec. 21, 1995

[30] Foreign Application Priority Data

Jun. 10, 1994 [DK] Denmark .................................. 0668/94

[51] Int. Cl.⁶ .................. C12P 35/00; C12P 35/04; C12P 35/02; C12P 35/06
[52] U.S. Cl. .................. 435/47; 435/45; 435/46; 435/50; 435/51; 435/49
[58] Field of Search .................. 435/41, 47, 45, 435/46–51

[56] References Cited

U.S. PATENT DOCUMENTS

| | | | |
|---|---|---|---|
| 5,268,271 | 12/1993 | Guisan Seijas et al. | 435/43 |
| 5,462,862 | 10/1995 | Groenen et al. | 435/69.1 |
| 5,525,483 | 6/1996 | Kaasgaard et al. | 435/45 |

OTHER PUBLICATIONS

Briggs et al. New J. Chem vol. 18(3) pp. 425–434, 1994 Abstract.

Segel. Enzyme Kinetics, p. 299 1975.

McDougall et al. Enzyme Microb. Technol. 1982 vol. 4, pp. 114–115.

*Primary Examiner*—Leon B. Lankford, Jr.
*Assistant Examiner*—Christopher R. Tate
*Attorney, Agent, or Firm*—Bierman, Muserlian and Lucas

[57] ABSTRACT

A method for providing a semisynthetic β-lactam antibiotic by enzyme catalyzed acylation of the parent β-lactam with an activated derivative of the side chain acid wherein a modulator, which consists of one or more compounds different from the reactants and the reaction product and which suppresses the hydrolysis of the activated derivative of the side chain acid and the desired product more than it suppresses the synthesis of the desired product, is added to the reaction mixture, at the beginning of the reaction process, in a concentration from about 0.2 to $100 \times 10^3$ μm.

14 Claims, No Drawings

1

ACYLATION METHOD FOR PENICILLINS AND CEPHALOSPORINS

TECHNICAL FIELD

The present invention relates to an improved method for enzymatic acylation. In particular, the invention relates to the preparation of β-lactam antibiotics by enzymatic acylation of the parent amino β-lactam moiety with an acylating agent which is an activated derivative of the side chain acid.

BACKGROUND ART

Enzymatic production of semisynthetic β-lactam antibiotics by acylation of the parent amino β-lactam moiety with the side chain acid or an activated derivative, such as an amide or an ester thereof, is known e.g. from West German patent application having publication No. 2,163,792, Austrian Patent No. 243,986, Dutch patent application No. 70-09138, West German patent application having publication No. 2,621,618, European patent application having publication No. 339,751, international patent application having publication No. WO 92/01061 and from international patent application having publication No. WO 93/12250.

From West German patent application having publication No. 3,507,403 it is known to add a lower aliphatic alcohol to the reaction mixture in order to improve the yield. According to said invention, the acylation is preferably carried out in a solvent which is water containing from about 5 to about 40 % (w/w) of methanol or ethanol. Presumably, the alcohol added lowers the activity of the water in the reaction mixture and thus the extent of the hydrolysis of the acylating agent and the desired product.

In the present specification, the moiety of the β-lactam antibiotic molecule which is a condensed ring system comprising a four-membered β-lactam ring which has an exocyclic amino group and a five- or six-membered ring with a sulphur atom in it and sharing a nitrogen atom with the β-lactam ring is referred to as the β-lactam moiety. The amino β-lactam obtained on deacylation of the exocyclic amino group is referred to as the parent amino β-lactam. Similarly, the acyl group to be introduced into the amino group of an amino β-lactam in order to produce a β-lactam antibiotic is referred to as the β-lactam side chain or just the side chain. The acid corresponding to the side chain is designated the side chain acid.

The parent amino β-lactams such as 6-aminopenicillanic acid (6-APA) and 7-aminodesacetoxycephalosporanic acid (7-ADCA) are commonly produced by enzymatic hydrolysis of a fermented penicillin (for example penicillin V or penicillin G). Besides impurities originating from the fermentation, the resulting crude solution typically contains unreacted traces of the β-lactam antibiotic used as starting material at a concentration of 150–200 mM. The crude solution can be purified and crystallized to obtain pure 6-APA or 7-ADCA (in the 7-ADCA case, the fermented penicillin has to go through a rearrangement process before the hydrolysis step).

A drawback of the known methods for enzymatic production of β-lactam antibiotics by acylation of the parent amino β-lactam with an activated derivative of the side chain acid is that under the reaction conditions used part of the acylating agent hydrolyses before it has reacted with the amino β-lactam. Thus, when the amide of the side chain acid is used as acylating agent, some free side chain acid and an equivalent amount of ammonia will be generated in the reaction mixture as a result of this hydrolysis. Similarly, when an ester of the side chain acid is used as acylating agent, some free side chain acid and an equivalent amount of the alcohol corresponding to the ester will be generated in the reaction mixture as a result of the hydrolysis. Also, the desired product formed hydrolyses to form free side chain acid and the parent amino β-lactam.

The loss of acylating agent and of the desired product due to hydrolysis leads to a reduced yield of the process, to a more laborious work up procedure and ultimately to an economy of the process which is less than optimal. Accordingly, it is desired to find a method of avoiding or reducing the loss of acylating agent and/or desired product.

SUMMARY OF THE INVENTION

It has now, surprisingly, been found that certain modulators, i.e. compounds different from the reactants and the reaction product, can be added to a reaction mixture in which enzymatic synthesis of a β-lactam antibiotic takes place in a concentration which is lower than that of the reactants, preferably lower than about 100 mM, to suppress the reaction in such a way that the hydrolysis of the acylating agent—when an activated derivative of the side chain acid is used as acylating agent—and of the desired product is suppressed more than the synthesis of the desired product.

Accordingly, in its broadest aspect the present invention relates to a method of providing a semisynthetic β-lactam antibiotic by enzymatic acylation of the parent β-lactam with an activated derivative of the side chain acid wherein a modulator which suppresses the hydrolysis of the acylating agent and the desired product more than it suppresses the synthesis of the desired product is added to or present in the reaction mixture.

Examples of β-lactam antibiotics which can be produced by the process of this invention are ampicillin, amoxicillin, ticarcillin, cefaclor, cefatrizine, cefaparol, cephradine, cephalexin, cefadroxil, cephaloglycin and cephalothin.

The acylating agent to be used in the method of this invention is an activated derivative of the side chain acid such as a lower alkyl (methyl, ethyl, n-propyl or isopropyl) ester or an amide. The amide can be unsubstituted in the —NH$_2$ group which is preferred, or it can be substituted by one or two lower alkyl groups—identical or different—selected from the group comprising methyl, ethyl, propyl and isopropyl. The derivative may be used in the form of a salt, for example, the hydrochloride or the sulphate. Examples of side chain acids are D-phenylglycine or D-p-hydroxyphenylglycine.

Examples of parent amino β-lactams which can be acylated by the method of this invention are 6-aminopenicillanic acid (6-APA), 7-aminodesacetoxycephalosporanic acid (7-ADCA), 7-aminocephalosporanic acid (7-ACA) and 7-amino-3-chloro-3-cephem-4-carboxylate.

Examples of modulators are given in the examples and in the claims.

DETAILED DESCRIPTION OF THE INVENTION

The method of the present invention can be used in combination with suitable methods of the known art. Thus, it can, for example, be combined with the methods described in international patent application having publication No. WO 92/01061 and in international patent application having publication No. WO 93/12250. The contents of both of said applications is hereby incorporated in its entirety by reference.

The amount of modulator to be added to the reaction mixture in order to achieve the desired effect depends i.a. on the identity of the modulator and on the amount of enzyme present in the reaction mixture. Some guidance to this can be found in the examples and in the claims. It is thus important to notice that a too high concentration of the modulator will prevent the desired reaction from taking place. Under all circumstances the useful concentration of modulator in the reaction mixture is so low that it does not influence the water activity in the reaction mixture. In any case, it will be lower than that of the reactants, preferably lower than 100 mM.

The enzyme to be used in the process of this invention may be any enzyme catalyzing the reaction in question. Such enzymes have been known since around 1966. Enzymes to be used are, for example, termed penicillin amidase or penicillin acylase and classified as E.C. 3.5.1.11. A number of microbial enzymes are known to have this activity, derived from for example Acetobacter, Xanthomonas, Mycoplana, Protaminobacter, Aeromonas (West German patent application having publication No. 2,163,792) Pseudomonas (Austrian Patent No. 243986), Flavobacterium (Dutch patent application No. 70-09138), Aphanocladium, Cephalosporium (West German patent application having publication No. 2,621,618), *Acetobacter pasteurianum, Bacillus megaterium, Xanthomonas citrii* (European patent application having publication No. 339, 751), *Kluyvera citrophila* (Agr.Biol.Chem. 37 (1973), 2797–2804) and *Escherichia coli* (West German patent application having publication No. 2,930,794). The *Escherichia coli* enzyme is commercially available. The enzyme may also be a so-called ampicillin hydrolase, acylase or amidase. In this connection, reference is, inter alia, made to Hakko to Kogyo 38 (1980), 216 et seq., the contents of which is incorporated by reference.

It is preferred to use the enzyme in a reusable form, for example, in entrapped or immobilized form. Immobilization may be done by any known method. Immobilized *Escherichia coli* enzyme is commercially available from Boehringer Mannheim GmbH, Germany, under the trade name Enzygel.

The process of this invention is generally carried out in a system containing water. If desired, an organic solvent may be added.

The solubility of the acylating agent such as the D-phenylglycine or D-p-hydroxyphenylglycine derivative or originating from the D,L mixtures as described in EP-A-339751, will vary with the identity of the derivative and with the composition of the reaction medium. In an aqueous system as used in the examples, the solubility of the hydrochloride of D-phenylglycine amide is typically approximately 450 mM. However, the solubility is very dependent on the salt components in the solution, as well as on the pH value and the temperature of the solution. In some embodiments of the process of this invention, the initial reaction mixture is a slurry containing undissolved acylating agent and/or amino β-lactam, which will dissolve partly or fully during the course of the reaction. The β-lactam antibiotic formed may precipitate during the reaction and, also, the hydrolysis products of the acylating agent such as D-phenylglycine and D-p-hydroxyphenylglycine, may precipitate. Hence, in some cases the reaction mixture will be a slurry throughout the duration of the reaction.

The amino β-lactam, for example 6-APA or 7-ADCA, used in the process of this invention may be obtained by enzymatic hydrolysis of the fermented penicillins or cephalosporins (for example penicillin V, penicillin G or cephalosporin C), or their ring enlarged analogues (for example V-DCA and G-DCA) or derivatives thereof followed by removal of the hydrolysis by-product, if desired (phenoxyacetic acid etc.). In some cases, the crude solution can be used directly without further purification or dilution.

Generally, the reaction temperature of the process of this invention may vary between about 0° C. and about 35° C., especially between about 5° C. and about 30° C. Temperatures in the range about 20°–30° C. may be preferred for convenient operation. The pH value which is optimal depends on the type and purity of enzyme. Using *Escherichia coli* enzyme, the optimal pH value is typically in the range from about 5.5 to about 7.5, preferably in the range from about 6.1 to about 7. For the preparation of amoxicillin, a pH value in the range from about 5.5 to about 6.4 is preferred. Control of the pH value may be used. Suitable reaction times are from several minutes to several hours, in particular from about ½ hour to about 8 hours. Suitable enzyme concentrations may be from about 1 U/ml to about 100 U/ml (1 U=one unit of enzyme activity, see below).

Using the method according to this invention, unusually high yields of the desired β-lactam antibiotic can be obtained. The high yields are obtained using the teachings of this invention and properly selecting the concentration of the acylating agent, the ratio between the concentration of acylating agent and the starting amino β-lactam, the pH value, the enzyme and the identity and amount of modulator.

Recovery and purification of the product can be achieved by methods known per se, for example by crystallisation.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

DEFINITIONS AND METHODS OF ANALYSIS

Abbreviations

D-HPGA is D-p-hydroxyphenylglycine amide, D-HPG is D-p-hydroxyphenylglycine, 6-APA is 6-aminopenicillanic acid, Amox is amoxicillin, Phox is phenoxyacetic acid, and Phyl is phenylacetic acid.

$V_0$(Amox) is the initial velocity of Amox formation, and $V_0$(D-HPG) is the initial velocity of D-HPG formation, specified as μmoles/min/g enzyme, μmoles/min/ml reaction mixture, or nmoles/min/U (enzyme activity).

Enzyme Activity

The following definition of penicillin G acylase activity is used: one unit (U) corresponds to the amount of enzyme that hydrolyses per minute 1 μmole of penicillin G under standard conditions (5% penicillin G, 0.2M sodium phosphate buffer, pH 8.0, 28° C).

The Synthetic vs. Hydrolytic Ratio X

The ratio X is defined as the number of moles of D-HPGA consumed per mole of Amox produced. For practical use this can be transformed to X=1+moles D-HPG/moles Amox, wherein "moles D-HPG" is the molar amount of D-HPG produced by hydrolysis of the acylating agent and the desired product and "moles Amox" is the molar amount of Amox present in the reaction mixture. Thus, if X is 1 this means that only the desired synthesis takes place, no hydrolysis. If X is 2, this means that D-HPG and Amox are formed in equal amounts (on a molar basis). If X is 3, this means that twice as much D-HPG as Amox is present in the reaction mixture (on a molar basis). The ratio X can be calculated at any time during reaction, but in the following examples X is calculated at the reaction stop time, which is defined as the time at which 90 % of the theoretical yield of Amox is present in the reaction mixture (based on the inserted amount of 6-APA). Square brackets are used to designate molar concentrations.

HPLC Analysis of Reaction Components

Column: $C_{18}$, YMC 120 Å, 5 μm (4.6×250 mm)

Elution with mixture of 96% 25 mM sodium phosphate buffer, pH value 6.5 and 4% acetonitrile.

Flow: 1 ml/min.

Detection: UV at 230 nm

Preparation of samples for analysis: the samples taken from the reaction mixtures were diluted with 25 mM sodium phosphate buffer to 400 times their volume. At this dilution all samples were fully dissolved.

Retention times in minutes: 2.6 (D-HPG), 3.5 (D-HPGA), 5.0 (6-APA), 13.5 (Amox).

Standard Reaction Conditions

In Examples 1–8 the following standard conditions for enzymatic amoxicillin synthesis have been used (see patent application No. WO 92/01061 for further details):

[D-HPGA]$_{start}$=650 mM

[6-APA]$_{start}$=200 mM

Temp.=25° C.

pH=6.0

During the reactions, the pH value of the reaction mixtures was kept constant by titration with 2M sulphuric acid.

Representative samples of the reaction mixtures including solid constituents were taken at regular intervals during the reactions and analyzed by HPLC.

Example 1

Enzymatic Synthesis of Amoxicillin Using a Fixed Dosage of Immobilized Pen G Acylase and Varying the Phox Concentration in the Reaction Mixture from 2.6 to 61.7 μM Experiment A (reference)

A standard synthesis (immobilized penicillin G acylase from *E. coli*; enzyme dosing 8.6 U/ml) was carried out with no Phox added. The Phox level was 2.6 μM in the reaction mixture due to a residual Phox content of 0.0009% w/w in the 6-APA used. The results obtained are reported in Table 1.

Experiments B–E

Same conditions as in Experiment A were employed, except that Phox was added to the reaction mixture at the beginning of the experiment in amounts so that the concentrations specified in Table 1 were obtained. The results are reported in Table 1.

TABLE 1

| Experiment | [Phox] (μM) in reaction mixt. | Initial velocity (μmoles/min/g) $V_o$ (Amox) | $V_o$ (D-HPG) | X at reaction stop time | Reaction stop time (h) |
|---|---|---|---|---|---|
| A | 2.6 | 17.7 | 25.0 | 2.9 | 2.1 |
| B | 9.9 | 13.1 | 16.5 | 2.7 | 3.3 |
| C | 16.8 | 11.9 | 13.8 | 2.55 | 4.1 |
| D | 31.0 | 8.8 | 8.8 | 2.35 | 5.7 |
| E | 61.7 | 6.5 | 5.4 | 2.05 | 9.5 |

Example 2

Enzymatic Synthesis of Amoxicillin Using a Fixed Dosage of Immobilized Pen G Acylase and Varying the Phyl Concentration in the Reaction Mixture from 32.9 to 127 μM Experiment A (reference)

A standard synthesis (immobilized penicillin G acylase from *E. coli*; enzyme dosing 8.6 U/ml) was carried out with no Phyl added. The Phox level in the reaction mixture was 2.6 μM. The results are reported in Table 2.

Experiments B–D

Same conditions as in Experiment A were employed, except that Phyl was added to the reaction mixture at the beginning of the experiment in amounts so that the concentrations specified in Table 2 were obtained. The Phox background level was 2.6 μM. The results are reported in Table 2.

TABLE 2

| Experiment | [Phox] (μM) in reaction mixture | [Phyl] (μM) in reaction mixture | Initial velocity (μmoles/min/g) $V_o$ (Amox) | $V_o$ (D-HPG) | X at reaction stop time | Reaction stop time (h) |
|---|---|---|---|---|---|---|
| A | 2.6 | 0 | 17.7 | 25.0 | 2.9 | 2.1 |
| B | 2.6 | 32.9 | 10.8 | 13.8 | 2.7 | 4.2 |
| C | 2.6 | 63.3 | 8.1 | 8.8 | 2.5 | 5.1 |
| D | 2.6 | 127 | 5.2 | 5.4 | 2.2 | 5.8 |

Example 3

Enzymatic Synthesis of Amoxicillin Using Various Immobilized Preparations of Pen G Acylase and Varying the Phox Concentration in the Reaction Mixture from 2.6 to 56.8 μM Four different immobilized Pen G acylase preparations were used: a) immobilized penicillin G acylase from *E. coli*; enzyme dosing 8.6 U/ml; b) agarose based immobilizate, dosing 12.0 U/ml; c) immobilizate obtained from Recordati, dosing 12.0 U/ml; and d) immobilizate obtained from Boehringer Mannheim (experimental preparation), dosing 11.5 U/ml.

Each immobilizate was tested under standard synthesis conditions in presence of Phox 2.6, 28.4 and 56.8 μM, respectively. The results obtained are presented in Table 3.

TABLE 3

Ratio X at reaction stop time.

| Immobilizate | [Phox] (μM) in reaction mixture | | |
|---|---|---|---|
|  | 2.6 | 28.4 | 56.8 |
| a | 2.9 | 2.35 | 2.05 |
| b | 2.4 | 1.85 | 1.7 |
| c | 2.3 | 1.9 | 1.95 |
| d | 2.5 | 1.95 | 1.9 |

Example 4

Enzymatic Synthesis of Amoxicillin Using Varying Amounts of Enzyme and a Constant Concentration of Phox An agarose based penicillin G acylase immobilizate was employed in the following experiments. The immobilizate which was kept in water was drained of excess water on a filter by applying suction for 1 min. Phox was added to a concentration of 31 μM in the reaction mixture. The results are reported in Table 4.

TABLE 4

| Experiment | [Phox] (μM) in reaction mixture | Enzyme dosage (U/ml) | Initial velocity (μmoles/min/ml) | | X at stop time |
|---|---|---|---|---|---|
|  |  |  | $V_0$ (Amox) | $V_0$ (D-HPG) |  |
| A | 31 | 11.9 | 1.17 | 0.60 | 1.75 |
| B | 31 | 23.8 | 2.97 | 1.85 | 1.8 |
| C | 31 | 47.5 | 6.6 | ca. 5.6 | ca. 2.0 |

Example 5

Enzymatic Synthesis of Amoxicillin by Using Soluble Pen G Acylase (Two Different Suppliers) and Varying the Phox Concentration in the Reaction Mixture from 2.6 to 142 μM Soluble Pen G acylase preparations were obtained from Calbiochem. art. No. 516329, ca. 1500 U/ml, and from GBF, ca. 300 U/ml. An enzyme dosage of 60 or 61 U/ml were employed in the two series. The results are reported in Table 5.

TABLE 5

| Soluble Pen G acylase | Enzyme dosage (U/ml) | [Phox] (μM) in reaction mixture | Initial velocity (nmoles/min/U) | | X at reaction stop time |
|---|---|---|---|---|---|
|  |  |  | $V_0$ (Amox) | $V_0$ (D-HPG) |  |
| Calbiochem | 61 | 2.6 | 52.2 | 33.4 | 2.1 |
|  | 61 | 56.8 | 11.0 | 6.8 | 1.8 |
|  | 61 | 142 | 5.5 | ca. 4.4 | ca. 1.7 |
| GBF | 60 | 2.6 | 61.1 | 50.0 | 2.1 |
|  | 60 | 56.8 | 21.7 | 14.4 | 1.8 |
|  | 60 | 142 | 6.3 | 3.6 | 1.7 |

Example 6

Enzymatic Synthesis of Amoxicillin by Using Immobilized Pen G Acylase and Varying the Concentration of L-(+)-Mandelic Acid from 0.64 to 36.1 mM Experiment A (reference)

A standard synthesis (immobilized penicillin G acylase from *E. coli*; enzyme dosing 12.0 U/ml) was carried out with no L-(+)-mandelic acid added. The Phox background level was <0.6 μM in the reaction mixture. The results obtained are reported in Table 6.

Experiments B–G

Same conditions as in Experiment A were employed, except that L-(+)-mandelic acid was added to the reaction mixture at the beginning of the experiment in amounts as specified in Table 6. The results are reported in Table 6. A side product obtained was α-hydroxybenzylpenicillin.

TABLE 6

| Experiment | [L-(+)-Mandelic acid] (mM) in reaction mixture | Initial velocity (nmoles/min/U) | | X at reaction stop time | Reaction stop time (h) |
|---|---|---|---|---|---|
|  |  | $V_0$ (Amox) | $V_0$ (D-HPG) |  |  |
| A | 0 | 180 | 270 | 3.0 | 1.7 |
| B | 0.64 | 156 | 207 | 2.9 | 2.4 |
| C | 3.3 | 137 | 174 | 2.8 | 2.8 |
| D | 6.7 | 119 | 146 | 2.65 | 3.0 |
| E | 13.3 | 89 | 110 | 2.65 | 4.7 |
| F | 14.2 | 80 | 106 | 2.8 | 4.2 |
| G | 36.1 | 49 | 68 | 2.8 | 5.5 |

With respect to minimization of the ratio X, the optimal L-(+)-mandelic acid concentration under the conditions chosen are thus in the interval 3.3-14.2 mM.

Example 7

Enzymatic Synthesis of Amoxicillin by Using Immobilized Pen G Acylase and Varying the 2-Thiopheneacetic Acid Concentration from 0.03 to 0.3 mM in the Reaction Mixture Experiment A (reference)

A standard synthesis (Boehringer Mannheim immobilized penicillin G acylase, experimental preparation; enzyme dosing 12 U/ml) was carried out with no 2-thiopheneacetic acid added. The Phox background level in the reaction mixture was below 0.6 μM. The results obtained are reported in Table 7.

Experiments B–C

Same conditions as in Experiment A were employed, except that 2-thiopheneacetic acid was added to the reaction mixture at the beginning of the experiment in amounts as specified in Table 7. The results obtained are reported in Table 7.

TABLE 7

| Experiment | [Thiopheneacetic acid] (mM) in the reaction mixture | Initial velocity (μmoles/min/ml) | | X at reaction stop time | Reaction stop time (h) |
|---|---|---|---|---|---|
|  |  | $V_0$ (Amox) | $V_0$ (D-HPG) |  |  |
| A | 0 | 3.28 | 4.90 | 3.0 | 1.5 |
| B | 0.03 | 1.68 | 1.95 | 2.7 | 2.3 |
| C | 0.3 | 0.15 | 0.058 | 1.6 | 12 |

Example 8

Enzymatic Synthesis of Amoxicillin Using Immobilized Pen G Acylase and Various Enzyme Modulators The compounds listed below improve synthesis performance (standard synthesis conditions, immobilized penicillin G acylase from *E. coli*; enzyme dosing 13 U/ml) in the sense that when they are present in the reaction mixture in a concentration within the interval specified, synthesis of the desired β-lactam antibiotic is favoured as compared to hydrolysis of the acylating agent:

| Concentration interval where improvement of ratio X is found | |
|---|---|
| Penicillin G | 2–1000 μM |
| Penicillin V | 2–1000 μm |
| Penicillin G sulfoxide | 2–500 μM |
| p-Hydroxyphenoxyacetic acid | 2–500 μM |
| (Phenylthio)acetic acid | 2–1000 μM |
| 2-Hydroxy-5-nitrobenzyl bromide | 10–500 μM |
| Phenylmethylsulfonyl fluoride | 0.2–10 μM |

We claim:

1. A method for providing a semisynthetic β-lactam antibiotic by enzyme catalyzed acylation of the parent β-lactam with an amide or ester of the side chain acid wherein a modulator, which is a carboxylic acid of 2 to 20 carbon atoms, and is different from the reactants and the reaction product is added to the reaction mixture, at the beginning of the reaction process, in a concentration from about 0.2 to 100×10$^3$ μm.

2. The method according to claim 1 wherein the acylating agent is the amide or a substituted amide of the side chain acid.

3. The method according to claim 1 wherein the acylating agent is selected from the group consisting of methyl-, ethyl-, propyl- and isopropyl ester of the side chain acid.

4. The method according to claim 1 wherein the modulator is a substituted acetic acid which further comprises an aromatic or a heteroaromatic ring either of which may be substituted or a functional derivative thereof.

5. The method of claim 4 wherein the functional derivative of the acid is an ester, an amide, a substituted amide or a hydrazide.

6. The method according to claim 1 or 4 wherein the functional derivative of the acid is selected from the croup consisting of an ester, an amide, a substituted amide and a hydrazide.

7. The method according to claim 1 wherein the modulator is selected from the group consisting of phenylacetic acid, (phenylthio)acetic acid, Penicillin G and Penicillin V.

8. The method according to claim 7 wherein the modulator is used in a concentration of from 2 to 2000 μM.

9. The method according to claim 1 wherein the modulator is selected from the group consisting of phenoxyacetic acid, p-hydroxyphenoxyacetic acid and Penicillin G sulfoxide.

10. The method according to claim 1 wherein the modulator is used in a concentration of from 2 to 1000 μM.

11. The method according to claim 1 wherein the modulator is mandelic acid.

12. The method according to claim 11 wherein the modulator is used in a concentration of from 0.05 to 100 mM.

13. The method according to claim 1 wherein the modulator is 2-thiopheneacetic acid.

14. The method according to claim 13 wherein the modulator is used in a concentration of from 0.003 to 10 mM.

* * * * *